United States Patent [19]

Imran

[11] Patent Number: 5,497,784
[45] Date of Patent: Mar. 12, 1996

[54] FLEXIBLE ELONGATE DEVICE HAVING STEERABLE DISTAL EXTREMITY

[75] Inventor: Mir Imran, Palo Alto, Calif.

[73] Assignee: Intelliwire, Inc., Sunnyvale, Calif.

[21] Appl. No.: 268,713

[22] Filed: Jun. 30, 1994

Related U.S. Application Data

[63] Continuation of Ser. No. 30,861, Mar. 12, 1993, abandoned, which is a continuation of Ser. No. 793,858, Nov. 11, 1991, Pat. No. 5,238,005.

[51] Int. Cl.[6] ...................................................... A61B 5/00
[52] U.S. Cl. ............................. 128/772; 604/95; 604/281
[58] Field of Search .................................. 128/772, 657, 128/658, 4, 6; 604/95, 164, 280, 281, 282

[56] References Cited

U.S. PATENT DOCUMENTS

| | | |
|---|---|---|
| 3,890,977 | 6/1975 | Wilson . |
| 4,737,142 | 4/1988 | Heckele ....................................... 604/95 |
| 4,753,223 | 6/1988 | Bremer ........................................ 128/4 |
| 4,758,222 | 7/1988 | McCoy ........................................ 604/95 |
| 4,776,844 | 10/1988 | Ueda ............................................ 604/95 |
| 4,799,474 | 1/1989 | Ueda ............................................ 128/4 |
| 4,884,557 | 12/1989 | Takehana et al. ......................... 128/4 |
| 4,921,482 | 5/1990 | Hammerslag et al. .................... 604/95 |
| 4,934,340 | 6/1990 | Ebling et al. ............................... 128/6 |
| 4,940,064 | 7/1990 | Desai .......................................... 128/784 |
| 4,944,727 | 7/1990 | McCoy ........................................ 604/95 |
| 4,977,886 | 12/1990 | Takehana et al. ......................... 128/4 |
| 5,037,391 | 8/1991 | Hammerslag et al. .................... 604/95 |
| 5,045,061 | 9/1991 | Seifert et al. .............................. 604/96 |
| 5,078,684 | 1/1992 | Yasuda ........................................ 604/95 |
| 5,095,915 | 3/1992 | Engelson .................................... 128/772 |

Primary Examiner—Stephen C. Pellegrino
Assistant Examiner—Guy V. Tucker
Attorney, Agent, or Firm—Flehr, Hohbach, Test, Albritton & Herbert

[57] ABSTRACT

Steerable flexible elongate device comprising a flexible elongate member having proximal distal extremities and having a centrally disposed lumen extending into the distal extremity. The flexible elongate member has at least three additional lumens spaced apart circumferentially about the centrally disposed lumen and extending into the distal extremity. A stiffener element is disposed in the centrally disposed lumen and has proximal and distal extremities. Additional flexible elongate elements having a negative coefficient of expansion are disposed in each of the three additional lumens and have proximal and distal extremities. The distal extremities of the stiffener element and the additional flexible elongate elements are secured to the distal extremity of the flexible elongate member. The proximal extremities of the stiffener element and the additional flexible elongate elements are also secured relative to the distal extremity of the flexible elongate member.

1 Claim, 6 Drawing Sheets

FLEXIBLE ELONGATE DEVICE HAVING STEERABLE DISTAL EXTREMITY

This is a continuation of Ser. No. 08/030,861, filed Mar. 12, 1993, now abandoned, which is a continuation of Ser. No. 07/793,858, filed Nov. 11, 1991, now U.S. Pat. No. 5,238,005.

This invention relates to a flexible elongate device having a steerable distal extremity and an apparatus for use therewith and method and more particularly to such a device which can be in the form of a steerable guide wire or a steerable catheter.

Steerable catheters and the guide wires have heretofore been provided, however, the steerability of the distal extremities of these guide wires and catheters has been very limited and difficult to control. There is therefore a need for a new and improved and flexible elongate device which can be in the form of a guide wire or catheter which has exceptional steerability characteristics at its distal extremities.

In general, it is obvious that the present invention is to provide a flexible elongate device having a steerable distal extremity and an apparatus for use therewith and a method.

Another object of the invention is to provide a device of the above character which can be in the form of a guide wire.

Another object of the invention is to provide a device of the above character which can be in the form of a catheter.

Another object of the invention is to provide a device of the above character in which the catheter can be a balloon dilatation catheter.

Another object of the invention is to provide a device of the character in which the steering of the distal extremity can be controlled by the use of a joystick and in which the distal extremity follows the movements of the joystick.

Another object of the invention is to provide a device of the above character in which a stiffening wire is utilized.

Another object of the invention is to provide a device of the above character in which the stiffening wire is provided with one or more hinge points in its distal extremity to make possible different types of bends in the distal extremity of the device.

Another object of the invention is to provide a device of the above character in which the bend in the distal extremity is proportional to the movement of the joystick.

Another object of the invention is to provide a device of the above character in which the bending of the distal extremity is achieved by the use of shape memory wires having a negative coefficient of resistance.

Another object of the invention is to provide a device of the above character in which the changes in the negative resistance of the wires are measured to predict the amount of movement of the distal extremity of the device.

Another object of the invention is to provide a device of the above character in which compensation is provided for differences in the negative coefficient of resistance in the shape memory wires of a device.

Another object of the invention is to provide a device of the above character in which the amount of bending of the distal extremity is controlled in accordance with the movement of the joystick.

Additional objects and features of the invention will appear from the following description in which the preferred embodiments are set forth in conjunction with the accompanying drawings.

In general, the steerable flexible elongate device incorporating the present invention is comprised of a flexible elongate member having proximal and distal extremities. The flexible elongate member is provided with a centrally disposed lumen extending into the distal extremity thereof and at least three additional lumens spaced apart circumferentially about the centrally disposed lumen and extending into the distal extremity of the flexible elongate member. A stiffening wire is disposed in the central lumen and has proximal and distal extremities. Means is provided for securing the distal extremity of the stiffening wire to the distal extremity of the flexible elongate member and for securing the proximal extremity of the stiffening wire to the proximal extremity of the flexible elongate member. Additional flexible elongate shape memory wires having a negative coefficient of resistance are disposed in each of the three additional lumens and have proximal and distal extremities. Means is provided for securing the proximal and distal extremities of the additional flexible elongate elements to the proximal and distal extremities of the flexible elongate member.

Figures 1, 1A:
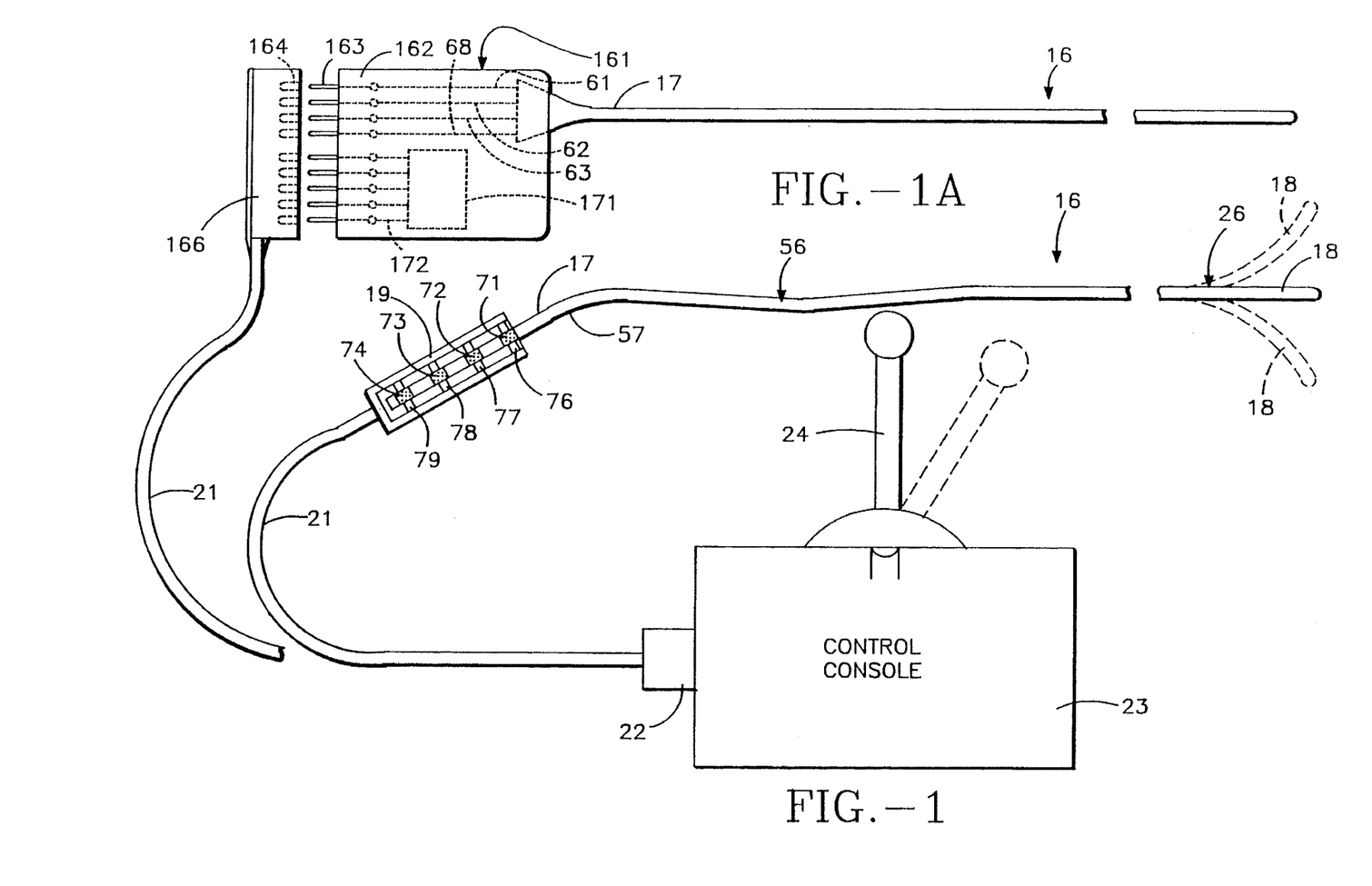
FIG. 1 is a side elevational view of a flexible elongate device having a steerable distal extremity incorporating the present invention and connected to a joystick control apparatus for controlling the same.
FIG. 1A is a side elevational view of another embodiment of a device incorporating the present invention.

More in particular, the steerable flexible elongate device 16 is provided with proximal and distal extremities 17 and 18 and has its proximal extremity 17 mounted in a connector 19. The connector 19 is connected to a cable 21 which is connected to another connector 22 mounted in a control console 23 having a pivotally mounted joystick 24 thereon. The joystick 24 is movable from a normal position to various positions within a cone having a center axis extending along the direction of the joystick 24 to cause movement of the distal extremity or tip 18 of the device 16 in accordance with the movement of the joystick 24 as hereinafter described.

Figure 2:
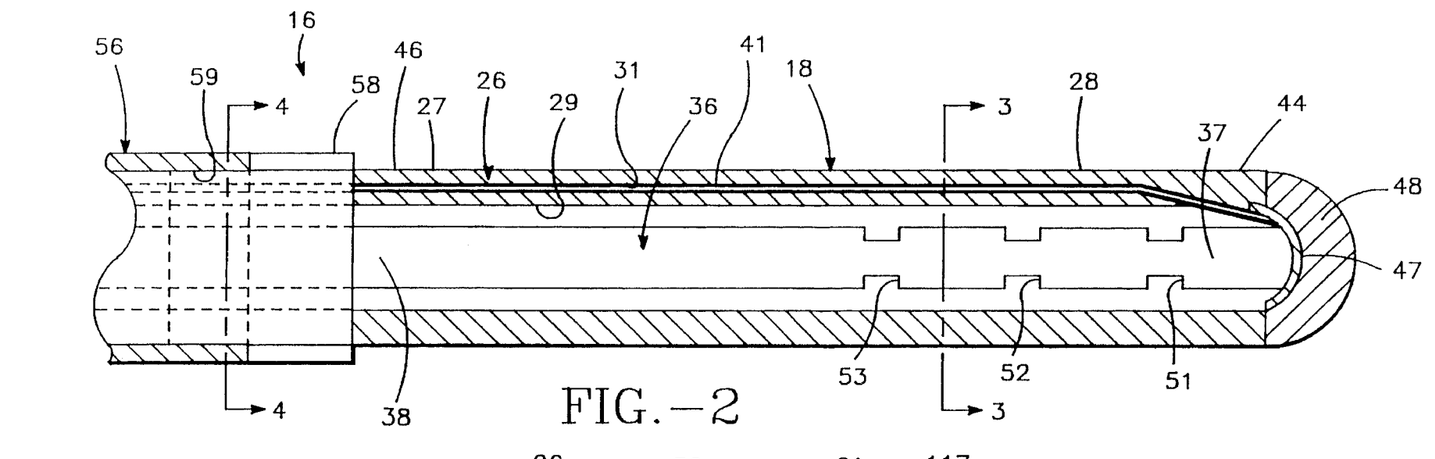
FIG. 2 is an enlarged detail view of the distal extremity of the flexible elongate device shown in FIG. 1.
Figure 3:
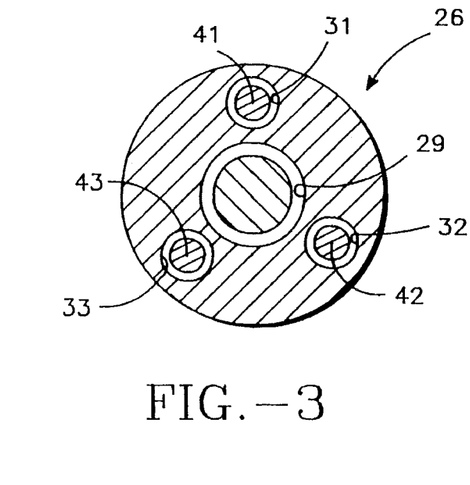
FIG. 3 is a cross-sectional view taken along line 3—3 of FIG. 2.

The flexible elongate device 16 in FIGS. 1 and 2 is shown in the form of a guide wire, the distal extremity or tip 18 of which is shown in enlarged cross-sectional form in FIG. 2. The distal extremity 18 is comprised of flexible elongate member 26 formed of a suitable plastic such as polyethylene, polyamide or silicone. It can be cylindrical in form and has proximal and distal extremities 27 and 28. The flexible elongate member 26 is provided with a centrally disposed lumen 29 which extends substantially the entire length of the member 26 to the distal extremity 28. The centrally disposed lumen 29 can have a suitable size as for example, from 0.002" to 0.010" and preferably a diameter of approximately 0.004". The flexible elongate member 26 is provided with at least three additional lumens 31, 32 and 33 which are spaced apart circumferentially about the centrally disposed lumen 27 and which also extend through the length of the flexible elongate member 26. They can have a suitable size as for example, ranging from 0.0015" to 0.004" and preferably a diameter of 0.0025". With such sizing of the lumens 27, 31, 32, 33 it can be seen that the overall diameter of the flexible elongate member 26 can be 0.010" or less so that it provides a relatively small dimension in cross-section while still at the same time providing a web or wall extending between the lumens which is at least 0.0005" in wall thickness.

The flexible elongate member 26 when formed of a polyamide has very good desirable mechanical characteristics as for example, good strength as well as good temperature characteristics, i.e., the capability to withstand temperatures in the range of 70° C. to 120° C. By utilizing the smallest dimensions, it is possible to provide a flexible elongate member 26 in the form of a guide wire having an overall diameter ranging from 0.008" to 0.010".

In accordance with the present invention a stiffener element or wire 36 formed of a suitable material such as stainless steel is disposed in the central lumen 27. The stiffener wire 36 should be sized so it is slightly smaller than the lumen in which it is disposed. Thus for a lumen of 0.004" in diameter, a stiffener wire of a diameter 0.003" can be utilized which has a distal extremity 37 and a proximal extremity 38.

Three additional flexible elongate elements or wires 41, 42, 43 are provided in the three lumens 31, 32, 33. The wires 41, 42, 43 are formed of a material which has a negative coefficient of expansion for purposes hereinafter described. The size of the wires 41, 42 and 43 is selected in accordance with the pulling force which is to be generated by the wires as hereinafter described. The wires 41, 42, 43 have distal extremities 44 and proximal extremities 46. In the embodiment shown in FIGS. 2 and 3 and in which lumens 31, 32 and 33 are provided having a diameter of 0.0025", the wires 41, 42 and 43 can have a diameter of 0.002". For the other sizes of lumens, wires having diameters ranging from 0.001" to 0.010" can be utilized. One type of wire having a suitable negative coefficient of expansion is a nickel-titanium alloy manufactured and sold under the trademark Nitinol. The heating of the Nitinol wire changes its crystalline structure causing it to shorten itself or in other words to have a negative coefficient of expansion. As hereinafter described, the wires 41, 42, 43 serve as electrical conductors for electric current and have their distal extremities 44 connected to the distal extremity 37 of the stiffener wire 36 by a suitable means such as solder 47 or by spot welding so that the stiffener wire 36 can serve as a return conductor or a ground return. A rounded tip 48 is provided at the distal extremity 28 of the tubular member 26 and can be formed of a suitable material such as a conductive epoxy to augment the electrical connection between the wires 41, 42 and 43 and the ground return wire 36.

Figures 8, 10, 11, 12:
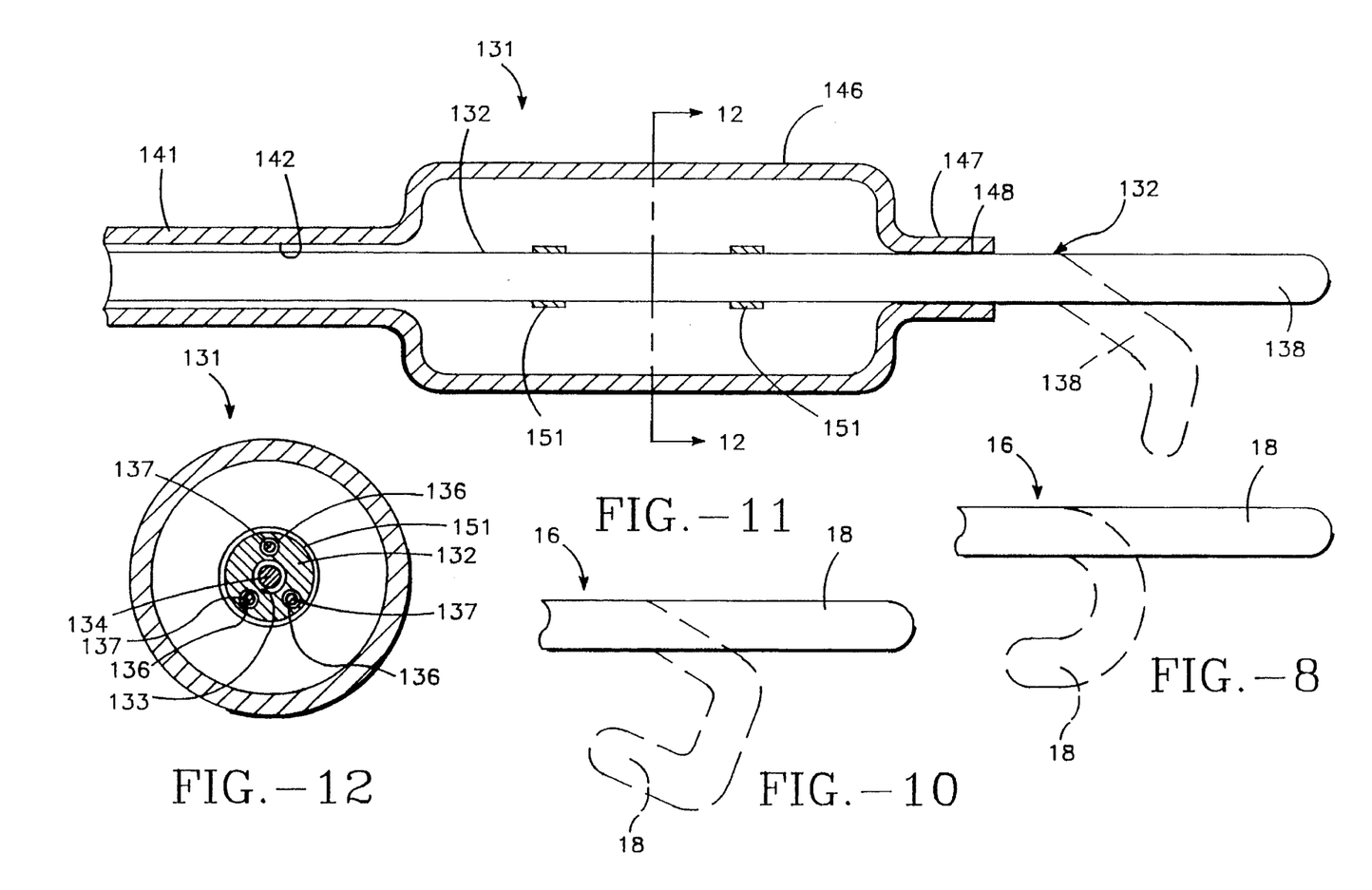
FIG. 8 is a partial side elevational view showing a flexible elongate device in the form of a guide wire and showing a bend which can be formed in the distal extremity thereof.
FIG. 10 is a side elevational view of the flexible elongate device in the form of a guide wire in which the distal extremity is bent into a compound bend.
FIG. 11 is a partial cross-sectional view showing a flexible elongate device incorporating another embodiment of the invention in the form of a balloon dilatation catheter.
FIG. 12 is a cross-sectional view taken along the line 12—12 of FIG. 11.

If desired, the stiffener wire 36 can be provided with one or more hinge points to facilitate the forming of bends having predetermined confirmations in the distal extremity of the device 16. Thus as shown in FIG. 2, hinge points have been provided which are spaced at various distances from the distal extremity 37 of the stiffener wire 36. These hinge points have been provided by forming annular grooves or recesses of various lengths. Thus by way of example, with a stiffener wire 36 of a diameter of 0.003", the annular grooves or recesses can be formed to a depth of 0.0005" so that the remaining portions of the stiffening wire within the grooves have a thickness of 0.002". The grooves or recesses 52, 52 and 53 can have various lengths extending along the axis of the stiffener wire 36 as for example, ranging from 0.0001" to 0.020" and various depths. With a single hinge point in the guide wire 36 it is possible to achieve a bend such as shown in FIG. 8 in all 360° in rotation.

It should be appreciated that different diameters on the stiffener wire can be provided to form hinge points in various manners. For example, the annular grooves or recesses can be formed by machining or grinding. They also can be formed by etching to reduce the diameter. Alternatively, the lengths of the stiffener wire between the hinge points can be increased in diameter by electroplating those annular regions by a suitable material such as nickel or chromium. Alternatively, those annular regions can be enamel coated.

The proximal extremity 27 of the flexible elongate member 26 is secured to another flexible elongate member 56 having proximal and distal extremities 57 and 58. The flexible elongate member 56 is provided with a single lumen 59 into which the proximal extremity 27 of the flexible elongate member 26 extends (FIG. 2) and is bonded therein by suitable means such as an adhesive or epoxy. The flexible elongate member 56 is also formed of a suitable plastic such as a polyamide although less heat sensitive materials such as polyethylene can be utilized since the Nitinol wires 41, 42 and 43 are not in contact with the same.

Figure 5:
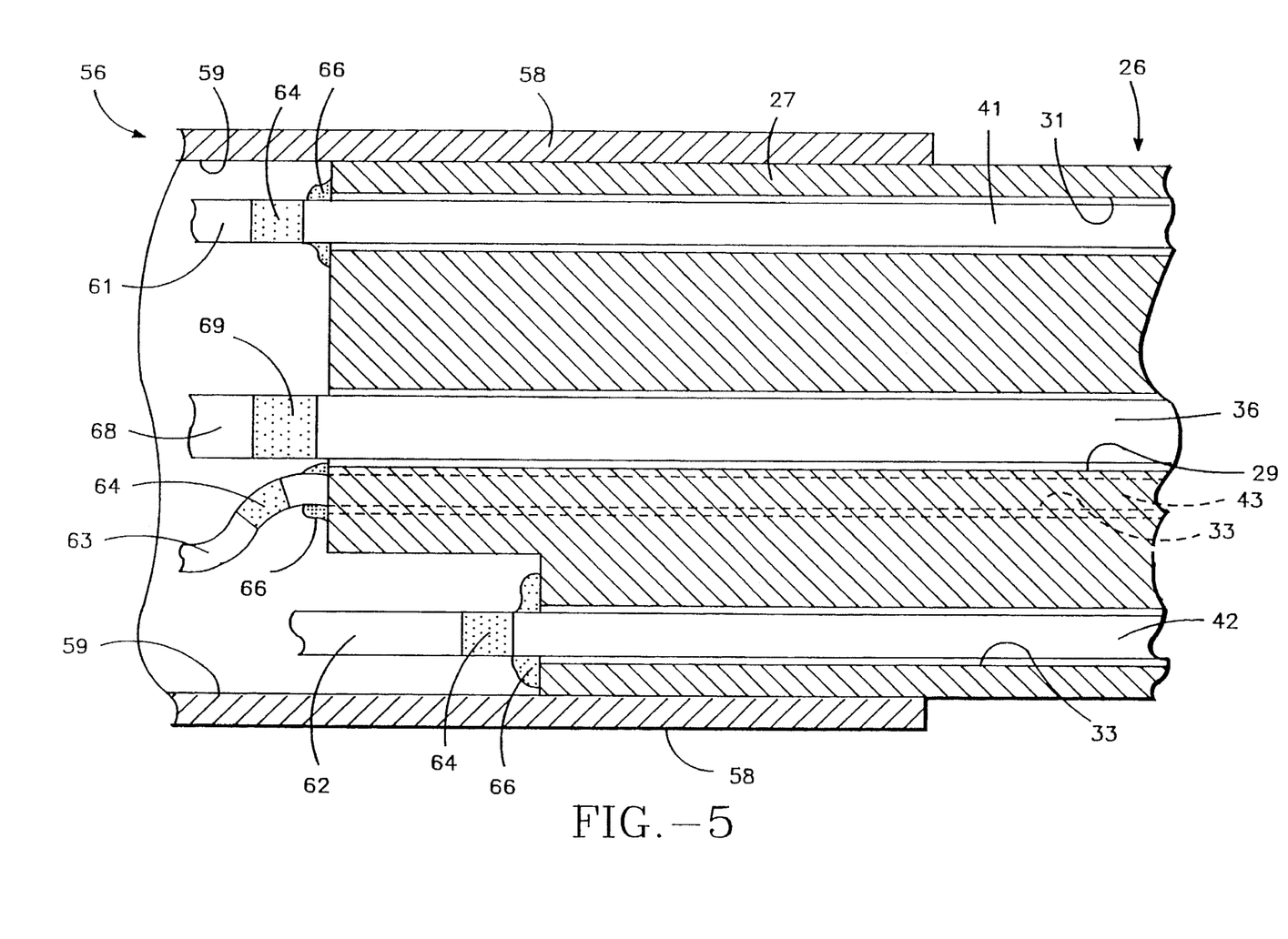
FIG. 5 is a greatly enlarged cross-sectional view of a portion of the flexible elongate device shown in FIG. 2.

The connection between the distal extremity 58 of the flexible elongate member 56 and the proximal extremity 27 of the flexible elongate member 26 is shown in detail in FIG. 5. Electrical conductors 61, 62, 63 are provided in the form of enameled copper wire which are bonded to the Nitinol wires 41, 42, 43 respectively by suitable means such as spot welded joints 64 and by providing an epoxy 66 which surrounds the joints 64. It should be noted that the spot weld joints 64 are offset longitudinally of the axis of the flexible elongate device 16 to facilitate making the spot weld joints 64 and also to prevent shorting of one spot weld joint to another. A support wire or core wire 68 is provided within the lumen 59 and is secured to the proximal extremity of the stiffener wire 36 by a spot weld joint 69. The support wire 68 can have the same size or a greater size than the stiffener wire 36 to provide the desired amount of rigidity in the flexible elongate device 16.

The conductors 61, 62, 63 and the support wire 68 extend to the proximal extremity 57 of the flexible elongate member 56 and also to the proximal extremity of the flexible elongate device 16 and are electrically connected to slip rings 71, 72, 73 and 74 mounted on the proximal extremity 57 and connected respectively to the conductors 61, 62 and 63 and to the support wire 68 to make electrical connections therewith. These slip rings 71, 72, 73, 74 are adapted to engage sleeves 76, 77, 78 and 79 respectively provided in the connector 19. These sleeves are connected by electrical conductors (not shown) provided in the cable 21 connected to the connector 22 mounted on the control console 23.

Figure 6:
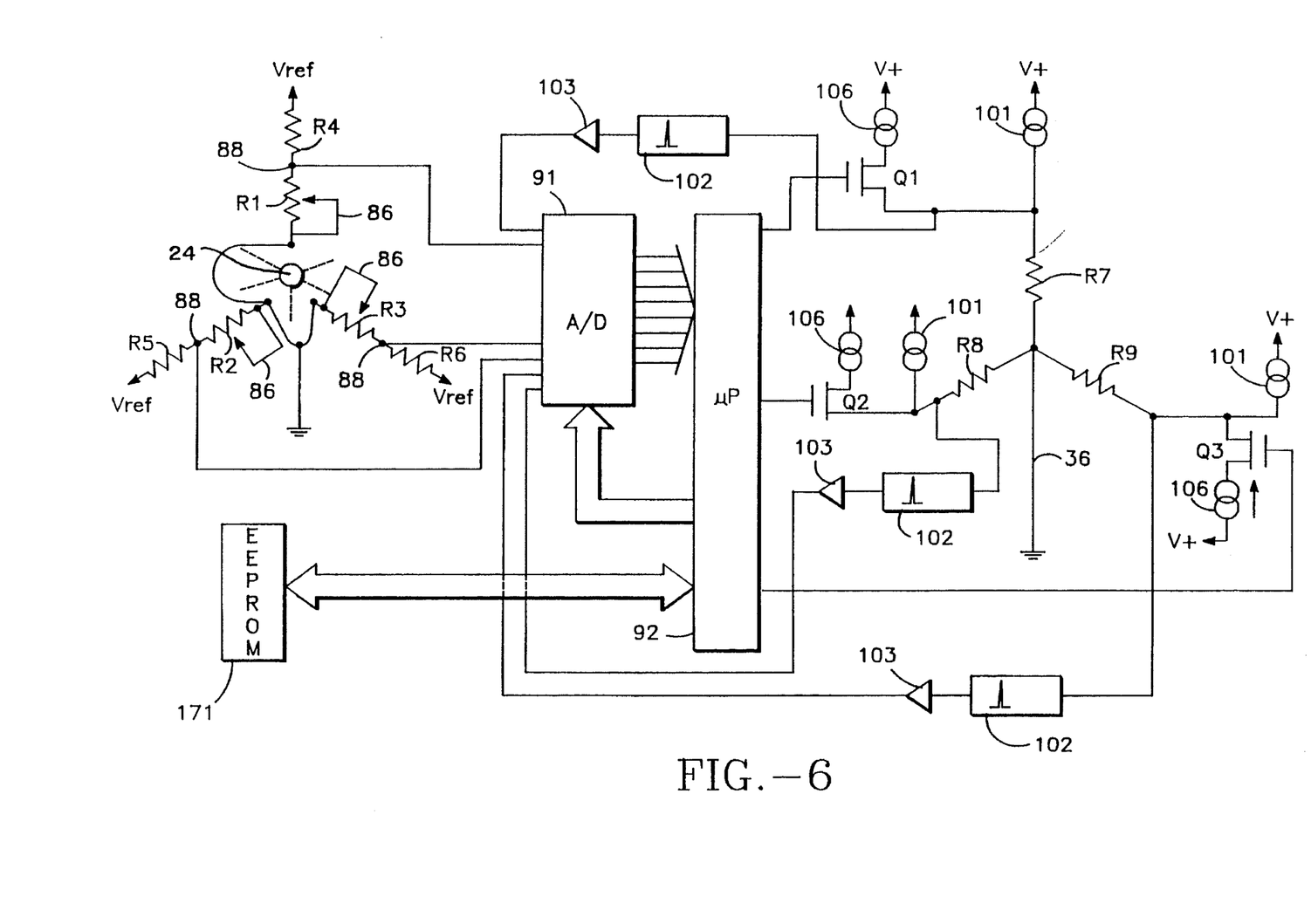
FIG. 6 is a block diagram showing the electronics for providing electronically steerable distal extremities for a flexible elongate device in the form of either a guide wire or catheter.

The joystick 24 controls electronic circuitry of the type shown in FIG. 6 which is mounted within the control console 23. The positioning of the joystick 24 controls the position of three wipers 86 which are associated with three potentiometers R1, R2, and R3. It has been found that by the use of the three potentiometers spaced 120° apart of the axis of the joystick 24, it is possible to precisely position the distal extremity 18 of the flexible elongate device 16 in accordance with the positioning of the joystick throughout all 360° of rotation within the cone in which the joystick can travel. The common points of the resistors R1, R2 and R3 of the three potentiometers are connected to ground as shown. Supply currents are supplied to the potentiometers R1, R2 and R3 through resistors R4, R5 and R6 from voltage reference sources identified as $V_{ref}$. The junctions 88 between these pairs of resistors provide analog signals in accordance with the position of the joystick 24 to an analog-to-digital converter 91 which by way of example can be a six-channel (A/D) converter. The output of the A/D converter 91 is supplied to a microprocessor 92. The Nitinol wires 41, 42 and 43 are represented schematically on the block diagram in FIG. 6 as resistor elements R7, RS, and R9 respectively in which the common points are joined together and connected to ground as shown, the ground is provided by the connections of the distal extremities of the wires 41, 42 and 43 to the distal extremity of the stiffener wire 36 as hereinbefore described so that the wire 36 serves as a ground return as hereinbefore described.

The microprocessor 92, which is connected to the Nitinol wires 41, 42 and 43 as represented by the resistors R7, R8, R9, is utilized for predicting the position of the distal extremity 18 of the flexible elongate device 16 with respect to a certain position of the joystick 24. Let it be assumed that the cone angle for the joystick 24 is 60° and that the joystick has been moved through one-half of the cone angle, as for example 30°, to achieve a bend in the distal extremity 18, which is one-half of the total bend which can be achieved. The desired bend is achieved by the passing current through one or more of the Nitinol wires 41, 42 and 43 to cause them to contract because of their negative coefficient of expansion to achieve bends in the distal extremity 18 as shown in dotted lines in FIG. 1.

Figure 7:
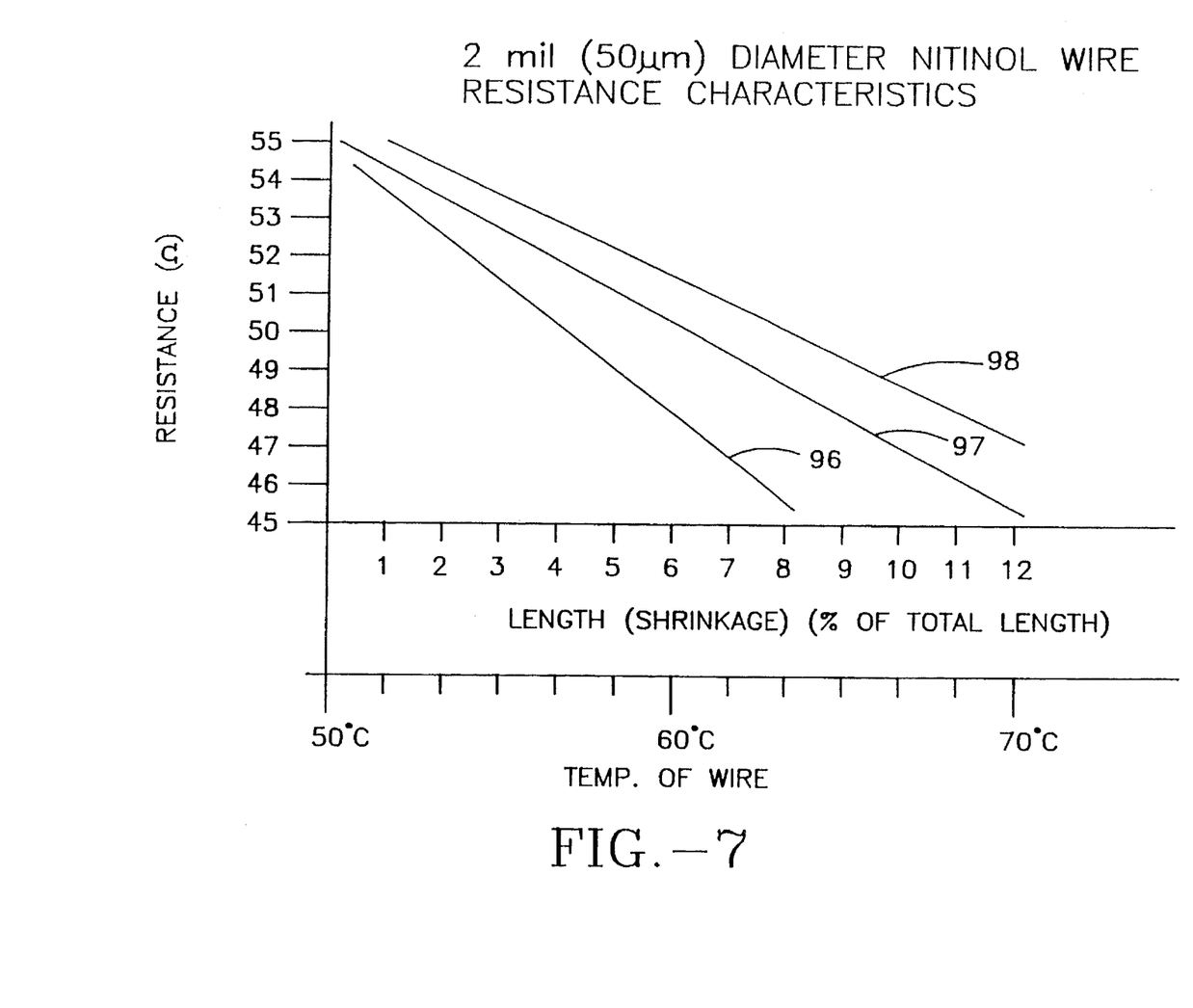
FIG. 7 is a graph showing the resistance characteristics of the wires utilized in the flexible elongate device of the present invention.

The shrinkage or contraction of the Nitinol wire with temperature is shown in FIG. 7. The Nitinol wires tested had a three-inch length and a diameter of 2 mils (0.002"). The straight lines 96, 97 and 98 in the graph in FIG. 7 shows the amount of shrinkage for three such wires as a percent of total length for a temperature ranging from 50° C. to 70° C. and with a resistance ranging from 45 to 55 ohms. It can be seen that the shrinkage is linear from the long relatively straight lines 96,. 97 and 98. It is this linear shrinkage characteristic which is utilized in the present invention.

Since the amount of bending of the distal extremity of the flexible elongate device 16 is predicated upon the amount of heating of the Nitinol wire, the resistance of the wire is measured to correlate that shrinkage with the movement of the joystick 24 and the bending of the distal extremity of the flexible elongate device 16. For that purpose, an RF source 101 of a high frequency ranging from 20 to 30 kHz at a constant current, as for example 50 microamperes, is used. This value of current is small enough so that it will not have any substantial effect on heating up of the Nitinol wire while still giving a meaningful signal which can be sensed by the microprocessor 92 to measure the resistance of the wires 41, 42 and 43. The AC signals produced represent the measured resistances of the Nitinol wires 41, 42 and 43 represented by the resistors R7, R8 and R9 in FIG. 6 are supplied through a narrow band filter 102 and an amplifier 103 to the input of a six-channel A/D converter 91. The microprocessor 92 samples the outputs from the amplifiers 103 which represent the changes of the position of the joystick 24 as the wiper 86 moves with respect to the associated potentiometers R1, R2 and R3. The microprocessor 92 ascertains what resistance should be found in the Nitinol wire associated with that resistor in accordance with the parameters provided by the graph shown in FIG. 7. The graph in FIG. 7 can be in the form of a lookup table in the microprocessor 92 or alternatively a formula in the microprocessor 92. The microprocessor 92 using this information turns on a switch which is identified as transistor Q1 for the resistor R7, Q2 for the resistor R8, and Q3 for the resistor R9 to allow the application of current from a constant current source 106, as for example, one providing a constant current of 50 milliamperes. The microprocessor 92 turns the transistors Q1, Q2 and Q3 on and off to provide a pulse width modulated signal creating a current signal, the duty cycle of which is controlled and is proportional to the resistance which it is desired to be achieved for that Nitinol wire. Since this resistance is being constantly sampled by the microprocessor 92, it is possible to precisely position the distal extremity of the flexible elongate device 16 and to stop the application of current when the desired bend has been reached in the distal extremity 18. If the Nitinol wire begins to cool down, this will also be sensed by the microprocessor 92 and additional current is supplied to the Nitinol wire to maintain it in a position in accordance with the position of the joystick 24. It is possible to provide a critically damped system so there is no undershoot or overshoot even though there may be some heat loss into the blood pool in which the device is disposed. By the use of a single joy stick 24 a simple bend such as shown in FIG. 18 can be provided in the distal extremity 18 of the catheter 16.

Figures 4, 9:
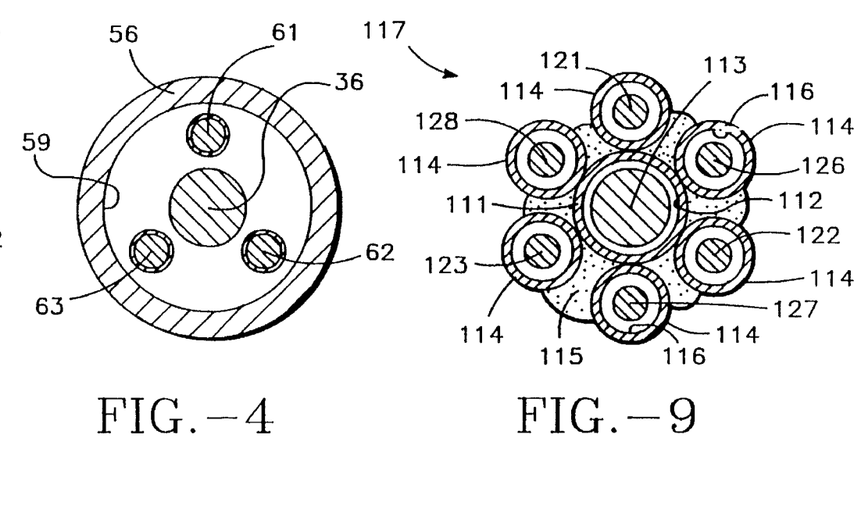
FIG. 4 is a cross-sectional view taken along line 4—4 of FIG. 2.
FIG. 9 is a cross-sectional view similar to FIG. 3, showing another embodiment of the present invention utilizing additional lumens.

In order to achieve more complex or compound bends in the distal extremity 18 of the catheter device 16, additional hinge points can be provided as shown in FIG. 2. The bends can be achieved by providing additional Nitinol pull wires and additional lumens such as shown in FIG. 9. As shown therein, the separate flexible elongate tubular member 111 is provided with a centrally disposed lumen 112 through which a stiffener wire 113 extends. A plurality of additional flexible elongate tubular members 114 are provided which have lumens 116 extending therethrough. By way of example as shown in FIG. 9, six of such flexible elongate members 114 can be provided and can be bonded around the outer circumference of the flexible elongate tubular member 111 by suitable means such an adhesive 115 to provide a unitary flexible elongate tubular assembly 117. Alternatively, the assembly can be mounted within another thin-walled tube (not shown). With such assemblies, a set of three pull wires each can be provided with the pull wires being spaced apart 120° circumferentially of the stiffener wire 113. Thus wires 121, 122 and 123 constitute one set of pull wires, and wires 126, 127, 128 constitute another set of pull wires. One set of these wires is connected to the stiffener wire 113 just distal of one of the hinge points about which it is desired to form a bend and the second set of Nitinol pull wires is attached just distal of another hinge point in the stiffener wire to cause bending around that hinge point. The two sets of pull wires are connected to two separate joysticks and the associated electronics of the type hereinbefore described to make it possible to create bending at two different hinge points to create a compound bend in the distal extremity 18 of the catheter device 16 such as that shown in FIG. 10.

From the foregoing it can be seen that the flexible elongate device having a steerable distal extremity of the present invention and the apparatus for use therewith and the method employed have many applications. They can be utilized for entering vessels in the human body for diagnostic and therapeutic purposes. For example, the coronary arteries and other coronary vessels of the heart can be readily navigated by the utilization of the joystick control, the position of which can be observed to guide the progress of the flexible elongate device as it is advanced into the vessels of the patient. Also, the distal extremity of the device can be observed fluoroscopically by the use of radiopaque markers (not shown) provided on the distal extremity of the device. By moving the joystick in the direction in which the distal extremity of the flexible elongate device is to extend, the device can be advanced through tortuous vessels with relative ease. The relatively small amount of heat which is created by the Nitinol wires to achieve the desired bending is readily dissipated by the blood flowing in the vessel of the patient without danger to the patient. Because of the microprocessor control utilized, it is possible for the physician or operator to position the joystick in a desired position and know that the distal extremity of the flexible elongate device will bend in accordance with the position of the joystick.

Although the foregoing description has been primarily in conjunction with a flexible elongate device in the form of a guide wire, it should be appreciated that the principles as set forth are applicable to many other types of elongate flexible devices, such as to guiding catheters, balloon dilatation catheters and the like, particularly when they are to be used to navigate tortuous vessels which are difficult to enter with conventional steerable guide wires and catheters.

The use of the present invention in conjunction with a steerable balloon dilatation catheter 31 is shown in FIGS. 11 and 12. It consists of a flexible elongate member 132 formed of a suitable plastic as hereinbefore described and which is provided with a centrally disposed lumen 133 having a stiffener wire 134 extending therethrough. It is also provided with at least three lumens 136 which are spaced circumferentially around the lumen 133 as for example, 120° apart from each other and have disposed therein Nitinol pull wires 137. The elongate member 132 is provided with a distal extremity 138.

Another elongate coaxial tubular member 141 is provided which has a lumen 142 therein through which the flexible elongate member 132 extends. The flexible elongate member 141 can be formed of a suitable material as for example, a heat shrinkable plastic. An inflatable balloon 146 is provided on the distal extremity of the flexible elongate member 141 and can be formed integral therewith or it can be formed as a separate balloon secured by an adhesive to the flexible elongate member 141. In FIG. 11, the balloon is shown being formed integral with the flexible elongate member 141 and has a distal extremity 147 bonded to the distal extremity of the flexible elongate member 132 by suitable means such as an adhesive 148.

As can be seen in FIG. 11, the balloon 146 is provided proximal of the distal extremity 138 of the flexible elongate member 132 so that the distal extremity of the flexible elongate member 132 can serve as a fixed guide wire for steering of the balloon dilatation catheter 131. The distal extremity 138 of the flexible elongate member 132 can be formed into a bend as shown by dotted lines by use of a joystick of the type hereinbefore described to facilitate advancing the balloon dilatation catheter 131 into tortuous vessels in the patient as for example, in the heart of the patient. Radiopaque markers 151 can be provided within the balloon on the flexible elongate member 132 to facilitate observing the positioning of the balloon in the vessel of the patient under X-ray fluoroscopy. When the balloon is in the desired position, the balloon 146 can be inflated by the introduction of liquid or a suitable gas through the balloon inflation lumen 142 to perform an angioplasty. After the angioplasty has been completed the balloon 146 can be deflated and the catheter 131 removed in a conventional manner.

As hereinbefore described and as shown in FIG. 7 in connection with the present invention, it has been found that different pieces of Nitinol wire may have different negative coefficients of expansion, even when taken from the same roll of wire. These typical differences are shown by the three straight lines 96, 97 and 98 in FIG. 7 which differences may represent several percent. In certain applications, it has been found desirable to compensate for these differences so that the joystick control as hereinbefore disclosed can provide precise control of distal extremity of the elongate device which it is intended to manuever. In order to accomplish this, a module 161 is provided into which the proximal extremity 17 of the flexible elongate device 16 is connected as shown in FIG. 1A. The module 161 includes a termination 162 which is provided with a plurality of male connectors mounted thereon which are adapted to be received by female connectors 164 provided in a connector block 166 that is connected to the cable 21. Cable 21 is connected to the control console 23 in the same manner as the cable 21 in FIG. 1. The conductors 61, 62 and 63 and the connector 68 are connected to the male terminals 163. A serial PROM or EEPROM 171 is provided within the module 161 and is connected by conductors 172 to additional male terminals 163. The EEPROM 171 is connected into the microprocessor 92 as shown in FIG. 6.

Operation and use of the serial PROM or the EEPROM 171 to compensate for the differences in the negative coefficients of expansion of the Nitinol wires 41, 42 and 43 can now be briefly described as follows. As soon as the elongate tubular device 16 has been manufactured as hereinbefore described, the distal extremity 18 is placed in the constant temperature bath, as for example, at a body temperature of 96.8° F. It is thereafter placed in another bath at a different temperature as for example at an elevated temperature 125° F. At each of these temperatures the resistance values of the three Nitinol wires 41, 42 and 43 are measured and recorded in the EEPROM 171. This information in the EEPROM 171 is available to the microprocessor 92 as shown in FIG. 6 and is utilized for making compensations so that for each incremental movement in any direction the joystick 24 is moved, the distal extremity 18 of the device 16 is moved the same incremental amount regardless of which Nitinol wire ie engaged. Thus, the microprocessor 92 using the resistance information stored in the EEPROM 171 compensates for any differences in the negative coefficients of expansion of the three Nitinol wires 41, 42 and 43.

Since the EEPROM 171 has been incorporated into the device 16 itself, the device 16 after manufacture will have information contained in EEPROM 171 for any variances in the negative coefficients of expansion in the Nitinol wires of the device so that it is unnecessary for the user of the same to make any further adjustments to accommodate any of the variances in the negative coefficients of expansion of the wires.

It should be appreciated that rather than producing analog signals from the joystick movement, it is possible to provide an optical joystick which would provide pulses giving a digital output rather than an analog output. For example, this can be accomplished by utilizing a rotating wheel having holes in it to make and break an optical link to provide digital light pulses which can be sensed electrically.

From the foregoing it can be seen that the present invention has excellent capabilities for the precise positioning of the distal extremities of flexible elongate elements or devices from remote locations under the control of a joystick to permit movement and to form bends in the distal extremity of the device throughout the entire 360° of rotation. The joystick control utilized makes it possible for the physician or operator to quickly learn how to precisely control the distal extremity of the flexible elongate device.

I claim:

1. In a method for controlling the distal extremity of a flexible elongate tubular member for movement in a vessel of a patient in accordance with a control member disposed outside of the vessel of the patient and being movable by hand, the distal extremity of the flexible elongate member having slidably disposed therein at least three circumferentially spaced apart flexible elongate pull elements formed of a material having a negative coefficient of expansion, the method comprising measuring resistance versus temperature characteristics of each of the pull elements outside of the vessel of the patient to provide measured information about each of the pull elements by placing the distal extremity of the flexible elongate tubular member in a constant temperature bath of one predetermined temperature, measuring the resistance of each of the pull elements while at said one predetermined temperature, placing the distal extremity of the flexible elongate tubular member in a constant temperature bath of another predetermined temperature and measuring the resistance of each of the pull elements while at said another predetermined temperature, storing the measured information about each of the pull elements at said one and said another predetermined temperatures and utilizing the stored measured information about each of the pull elements to cause movement of the distal extremity of the flexible elongate member in a proportional manner as the control member is moved.

* * * * *